United States Patent
Goto

(10) Patent No.: US 9,259,153 B2
(45) Date of Patent: Feb. 16, 2016

(54) ANTERIOR OCULAR SEGMENT TOMOGRAPHIC IMAGE ANALYSIS METHOD AND ANTERIOR OCULAR SEGMENT TOMOGRAPHIC IMAGE ANALYSIS APPARATUS

(71) Applicant: CANON KABUSHIKI KAISHA, Tokyo (JP)

(72) Inventor: Atsushi Goto, Miura-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 342 days.

(21) Appl. No.: 13/798,940

(22) Filed: Mar. 13, 2013

(65) Prior Publication Data
US 2013/0258280 A1    Oct. 3, 2013

(30) Foreign Application Priority Data

Mar. 30, 2012 (JP) ................. 2012-082211
Jan. 22, 2013 (JP) ................. 2013-009239

(51) Int. Cl.
*A61B 3/14* (2006.01)
*A61B 3/00* (2006.01)
*A61B 3/10* (2006.01)
*A61B 3/117* (2006.01)
*G06T 7/60* (2006.01)

(52) U.S. Cl.
CPC ............... *A61B 3/117* (2013.01); *A61B 3/102* (2013.01); *A61B 3/14* (2013.01); *G06T 7/60* (2013.01); *G06T 2207/10101* (2013.01); *G06T 2207/20101* (2013.01); *G06T 2207/30041* (2013.01)

(58) Field of Classification Search
CPC .......... A61B 3/14; A61B 3/103; A61B 3/113; A61B 3/1225; A61B 3/024; A61B 3/032; A61B 3/1015
USPC .......... 351/206, 200, 205, 210, 221, 222, 223, 351/246
See application file for complete search history.

(56) References Cited

FOREIGN PATENT DOCUMENTS

JP    2011-147611 A    8/2011

*Primary Examiner* — Dawayne A Pinkney
(74) *Attorney, Agent, or Firm* — Fitzpatrick, Cella, Harper & Scinto

(57) ABSTRACT

To determine an opening degree of a chamber angle with higher accuracy compared to that of a conventional technology, provided is an anterior ocular segment tomographic image analysis method including: a first determination step of determining an approximated line that approximates a shape of an anterior surface of an iris along the anterior surface of the iris in an anterior ocular segment tomographic image; a second determination step of determining an approximated line extended part obtained by extending the approximated line until the approximated line crosses a baseline in contact with an inner surface of a cornea and an inner surface of a sclera of an anterior ocular segment in the anterior ocular segment tomographic image; and a calculation step of calculating an opening degree of an anterior chamber angle of the anterior ocular segment through use of the approximated line and the approximated line extended part.

34 Claims, 3 Drawing Sheets

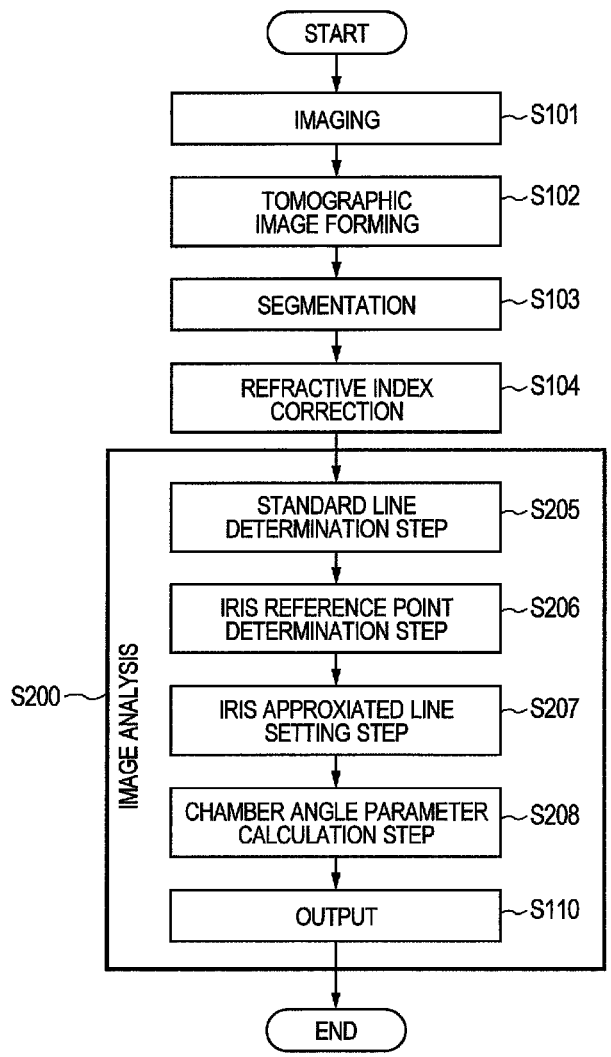

ANTERIOR OCULAR SEGMENT TOMOGRAPHIC IMAGE ANALYSIS METHOD AND ANTERIOR OCULAR SEGMENT TOMOGRAPHIC IMAGE ANALYSIS APPARATUS

BACKGROUND OF THE INVENTION

1. Field of the Invention

The present invention relates to an image processing apparatus for supporting diagnosis which is performed based on an image of an anterior ocular segment. Specifically, the present invention relates to an anterior ocular segment tomographic image analysis method and an anterior ocular segment tomographic image analysis apparatus to be used for performing diagnosis based on an acquired anterior ocular segment tomographic image.

2. Description of the Related Art

An optical coherence tomographic image acquiring apparatus for eyes, such as optical coherence tomography (OCT), is capable of three-dimensional observation of an internal state of a retina layer and a state of cornea of an anterior ocular segment. This optical coherence tomographic image acquiring apparatus has been receiving attention in recent years because the optical coherence tomographic image acquiring apparatus is useful for accurate diagnosis of a disease.

Japanese Patent Application Laid-Open No. 2011-147611 discloses a unit for easily determining multiple parameters for measuring an opening degree of a chamber angle based on an anterior ocular segment tomographic image, which includes a chamber angle region of an eye to be inspected and is obtained by the OCT, by causing an examiner to perform respective input operations through use of a graphic display while viewing the anterior ocular segment tomographic image displayed on a monitor. In this case, the examiner extends and turns an auxiliary line positioned on an anterior surface of an iris of an anterior ocular segment in the tomographic image and associates the auxiliary line with the tomographic image, thereby deducing a position of an angle recess even in the case where it is difficult to view the vicinity of the angle recess to determine the above-mentioned parameters.

By the way, in the case where an eye to be inspected has a symptom of narrow angle eye, the shape of an anterior surface of an iris of an anterior ocular segment is curved in some cases. In this case, with the procedure disclosed by Japanese Patent Application Laid-Open No. 2011-147611, there is a risk in that a region including the anterior surface of the iris of the anterior ocular segment as one side, which is to be required for calculating an opening degree of a chamber angle, may not be determined accurately. Specifically, in the case of the method disclosed by Japanese Patent Application Laid-Open No. 2011-147611, the anterior surface of the iris of the anterior ocular segment is approximated with a straight line, and hence, an opening degree of a chamber angle may be calculated as a value larger than a usual value. In this case, there is a risk in that a disease such as narrow angle eye that is required to be treated may be overlooked.

SUMMARY OF THE INVENTION

In view of the above, the present invention is to provide an anterior ocular segment tomographic image analysis method and an anterior ocular segment tomographic image analysis apparatus capable of determining an opening degree of a chamber angle with higher accuracy compared to that of the conventional technology.

In order to achieve the above-mentioned object, the present invention has a feature in the following configuration. Specifically, according to an exemplary embodiment of the present invention, there is provided an analysis method for analyzing an anterior ocular segment tomographic image of an eye to be inspected, the analysis method including:

determining an approximated line that approximates a shape of an anterior surface of an iris of an anterior ocular segment of the eye to be inspected along the anterior surface of the iris in the anterior ocular segment tomographic image;

determining an approximated line extended part obtained by extending the approximated line until the approximated line crosses a baseline in contact with an inner surface of a cornea and an inner surface of a sclera of the anterior ocular segment in the anterior ocular segment tomographic image; and calculating an opening degree of an anterior chamber angle of the anterior ocular segment through use of the approximated line and the approximated line extended part.

Further, according to another exemplary embodiment of the present invention, there is provided an analysis apparatus for analyzing an anterior ocular segment tomographic image of an eye to be inspected, the analysis apparatus including:

a first determination unit for determining an approximated line that approximates a shape of an anterior surface of an iris of an anterior ocular segment of the eye to be inspected along the anterior surface of the iris in the anterior ocular segment tomographic image;

a second determination unit for determining an approximated line extended part obtained by extending the approximated line until the approximated line crosses a baseline in contact with an inner surface of a cornea and an inner surface of a sclera of the anterior ocular segment in the anterior ocular segment tomographic image; and a calculation unit for calculating an opening degree of an anterior chamber angle of the anterior ocular segment through use of the approximated line and the approximated line extended part.

According to the present invention, the opening degree of the chamber angle can be determined with higher accuracy compared to that of the conventional technology.

Further features of the present invention will become apparent from the following description of exemplary embodiments with reference to the attached drawings.

BRIEF DESCRIPTION OF THE DRAWINGS

FIG. 2 is a flowchart illustrating an anterior ocular segment tomographic image analysis method to which the present invention is applied.

DESCRIPTION OF THE EMBODIMENTS

As an example of the present invention, an anterior ocular segment tomographic image analysis apparatus according to an embodiment of the present invention is hereinafter described in detail with reference to the drawings.

(Configuration of Entire Apparatus)

Figure 1:
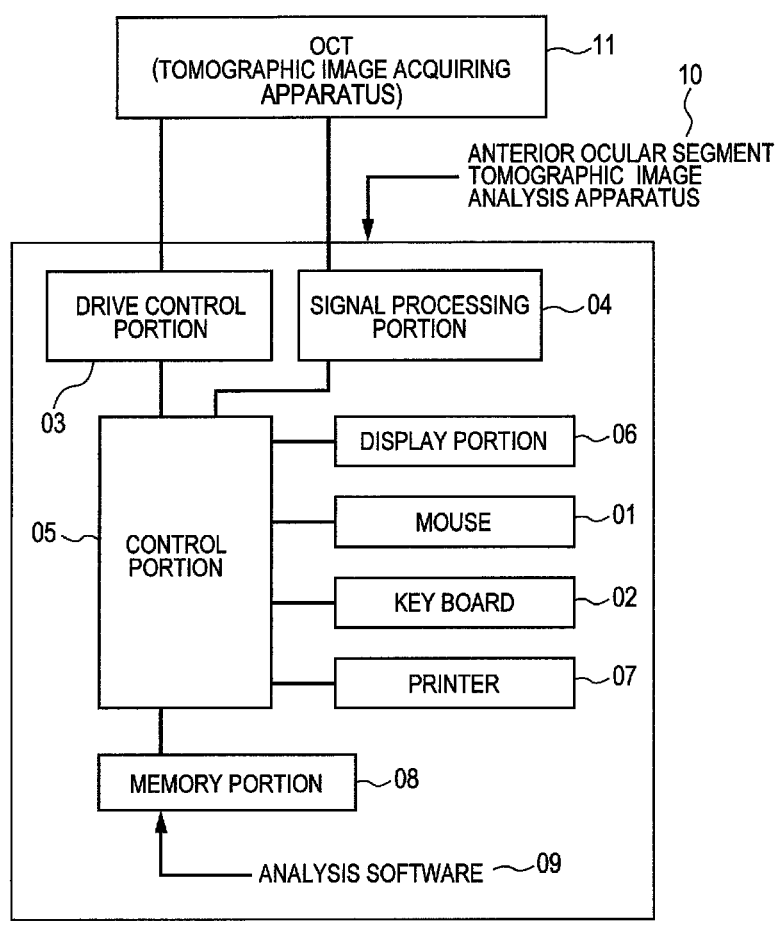
FIG. 1 is a block diagram illustrating a configuration of an anterior ocular segment tomographic image analysis apparatus according to an embodiment of the present invention.

FIG. 1 is a schematic view illustrating a configuration of the anterior ocular segment tomographic image analysis apparatus according to the embodiment of the present invention.

An anterior ocular segment tomographic image analysis apparatus 10 to be connected to an anterior ocular segment tomographic image acquiring apparatus 11 acquires information unique to an eye to be inspected. Note that, although an OCT is used as an example of the anterior ocular segment tomographic image acquiring apparatus 11 for acquiring an anterior ocular segment tomographic image in this embodiment, an anterior ocular segment shape imaging apparatus having a Scheimpflug camera mounted thereon or an ultrasonic biomicroscope (UBM) may be used instead.

(Example of Anterior Ocular Segment Tomographic Image Analysis Apparatus)

An example of the anterior ocular segment tomographic image analysis apparatus 10 is described. The anterior ocular segment tomographic image analysis apparatus 10 includes a mouse 01, a keyboard 02, a drive control portion 03, a signal processing portion 04, a control portion 05, a display portion 06, a printer 07, and a memory portion 08, and each portion is electrically connected to the control portion 05 through a bus or the like. The drive control portion 03, the signal processing portion 04, and the control portion 05 may be constructed integrally as a central processing unit (CPU), for example, so as to configure respective corresponding functional modules. The mouse 01 and the keyboard 02 are used as an operation input portion for the drive control portion 03 and as an example of an operation input portion for performing each determination of image processing through use of an anterior ocular segment tomographic image. Note that, a touch panel may be used as the operation input portion in the display portion 06.

The drive control portion 03 controls the anterior ocular segment tomographic image acquiring apparatus 11 based on an input from an operator, and the anterior ocular segment tomographic image acquiring apparatus 11 acquires an anterior ocular segment tomographic image.

The signal processing portion 04 forms an image, analyzes the formed image, and generates visualized information on the analysis result, based on a signal output from the OCT.

The control portion 05 controls the entire apparatus and displays the image or the like formed by the signal processing portion 04 on a display screen of the display portion 06.

The display portion 06 corresponds to an example of a display unit or a display apparatus. The display portion 06 is, for example, a liquid crystal display. The display portion 06 displays an acquired image formed by the signal processing portion 04 and the analysis result of the image based on a signal from the control portion 05.

The printer 07 prints the acquired image formed by the signal processing portion 04 and the analysis result of the image based on the signal from the control portion 05. The memory portion 08 stores the acquired image formed by the signal processing unit 04 and the analysis result of the image through the control portion 05. Further, analysis software 09 is installed on the memory portion 08, and the signal processing portion 04 accesses the memory portion 08 through the control portion 05 to run the analysis software 09. The memory portion 08 may be, for example, a hard disk drive (HDD).

The CPU including the above-mentioned control portion 05 performs analysis of an anterior ocular segment tomographic image based on an analysis program stored in the memory portion 08, and execution of the analysis program enables the use of the anterior ocular segment tomographic image analysis apparatus 10. The process of the analysis is performed based on the tomographic image stored in the memory portion 08 and a setting result by the mouse 01, and the result thereof is displayed on the display portion 06 in accordance with the analysis program. Further, the analysis program may be installed on a commercially available personal computer (PC) so that the PC includes an operation processing portion, an input portion, a memory portion, a display portion, and the like having the above-mentioned configuration.

(Processing Operation)

Next, a processing operation is described with reference to FIG. 2.

(Imaging: S101)

An operator operates the mouse 01 or the keyboard to send a signal from the control portion 05 to the drive control portion 03, thereby performing anterior ocular segment imaging by the OCT (anterior ocular segment tomographic image acquiring apparatus) 11. An interference signal obtained as a result of imaging is output to the signal processing portion 04.

(Tomographic Image Forming: S102)

The signal processing portion 04 subjects the interference signal output from the OCT to general reconfiguration processing to form a tomographic image.

First, the signal processing portion 04 removes a fixed pattern noise from the interference signal. The fixed pattern noise is removed, for example, by averaging multiple detected A-scan signals to extract a fixed pattern noise and subtracting the fixed pattern noise from the input interference signal.

Next, the signal processing portion 04 performs a desired window function processing so as to optimize a depth resolution and a dynamic range which are to have a tradeoff relationship in the case of Fourier transform in a finite interval.

Next, fast Fourier transform (FFT) is performed to form a tomographic image.

(Segmentation: S103)

The signal processing portion 04 performs segmentation of the tomographic image.

The signal processing portion 04 first uses a median filter and a Sobel filter respectively for the tomographic image to be processed so as to form images (hereinafter respectively referred to as a median image and a Sobel image). Next, a profile is formed from the generated median image and Sobel image for each A-scan. A brightness value profile is generated from the median image, and a gradient profile is generated from the Sobel image. Then, a peak in the profile generated from the Sobel image is detected. With reference to the profiles of the median image corresponding to before and after the detected peak or between peaks, a boundary of regions in the anterior ocular segment is extracted. Specifically, boundaries of an anterior surface of the cornea, a posterior surface of the cornea, an anterior surface of the iris, a posterior surface of the iris, and an anterior surface of the lens are extracted. Note that, in the case where it is difficult to view an angle recess, the boundary of the anterior surface of the iris is cut somewhere in the middle from a tip end of iris to the angle recess.

(Refractive Index Correction: S104)

The anterior ocular segment tomographic image acquired by the tomographic image forming contains image distortion caused by the fact that a speed of light traveling through a medium varies depending on a refractive index of the medium, and hence, the image distortion is eliminated by correcting the refractive index.

The refraction of light causing image distortion follows Snell's law, and hence, a space of the anterior ocular segment tomographic image is re-calculated in accordance with Snell's law to correct the refractive index to have a shape reflecting an entity. As refractive indices of a medium required for calculation, a refractive index of air of 1, a refractive index of a cornea of 1.377, and a refractive index of a hydatoid of 1.337 are used. Note that, the value of a refractive index of a medium can be adjusted, and another numerical value may be used.

(Image Analysis: S200)

The signal processing portion 04 performs image analysis with respect to the anterior ocular segment tomographic image subjected to refractive index correction.

An analysis procedure to be performed by the apparatus with respect to an anterior ocular segment tomographic image including a chamber angle region of an eye to be inspected is described below. FIGS. 3A to 3E are diagrams illustrating a specific example in the case of quantitatively analyzing a tomographic image of a chamber angle region of an eye to be inspected.

In FIGS. 3A to 3E, a region in an upper left part represents a cornea, a region in a lower left part represents an iris, and an area sandwiched by the cornea and the iris represents an anterior chamber. Although a chamber angle is positioned at a right end of the anterior chamber, the chamber angle does not clearly appear due to the problem of a light invasion depth of the OCT, and hence, segmentation cannot be performed. A region in a lower right part represents a sclera. Specifically, a cornea center is present on a left outer side of each figure. A curve extending from the uppermost part of each figure to the right represents a cross-section of a plane connected from the surface of the cornea to the surface of the sclera, and the second line on the left side of each figure presents an inner surface or a posterior surface of the cornea or sclera. Further, the third line on the left side of each figure represents an anterior surface of the iris (side surface of anterior chamber), and the fourth line on the left side of each figure represents an inner surface of the iris (posterior surface). An anterior chamber filled with an aqueous humor is present between the inner surface of the sclera and the anterior surface of the iris, and the chamber angle indicates a discharge portion of the aqueous humor present at an end of the anterior chamber positioned on an outer side of a scleral spur.

An anterior ocular segment tomographic image At processed in a data processing portion is displayed on the display portion 06.

The analysis program includes: a step of displaying an anterior ocular segment tomographic image on the display portion 06; a baseline determination step of determining a baseline (for example, a baseline SL) in contact with the inner surfaces of the cornea and the sclera in the anterior ocular segment tomographic image displayed on the display portion 06 and displaying the baseline on the display portion 06; an iris reference point determination step of determining an iris reference point (for example, a reference point R2) at which a normal to the baseline and the anterior surface of the iris cross each other; an iris approximated line setting step of determining an iris approximated line (for example, an approximated line KL) obtained by approximating the shape of the anterior surface of the iris from the iris reference point toward the angle recess and extending the approximated line until the approximated line crosses the baseline, and displaying the iris approximated line on a monitor; and a chamber angle opening degree calculation step of calculating an opening degree of an anterior chamber angle of an eye to be inspected through use of information on the iris reference point R2, the baseline SL, and the iris approximated line KL. In this embodiment, the iris approximated line and the like are set as needed in accordance with an eye to be inspected for calculating an opening degree, and an opening degree of the eye to be inspected is calculated and determined through use of the set approximated line and the like. However, in the present invention, the following description is made with these steps being interpreted as those for determining an approximated line and the like for convenience sake.

A specific analysis procedure is described below. In the following description, the case is described in which a baseline determination step S205, an iris reference point determination step S206, an iris approximated line setting step S207, and a chamber angle parameter calculation step S208 are performed successively in a divided manner.

The baseline determination step S205 includes: a step of determining a standard point S in an inner surfaces of the cornea and the sclera displayed on the display portion 06; a step of determining a cornea reference point R1 away from the standard point S by a predetermined distance along the posterior surface of the cornea; and a step of determining a line connecting the standard point S to the cornea reference point R1 as a baseline (baseline SL). First, an examiner operates the mouse 01 to determine a standard point S of quantitative analysis at the image At displayed on the display portion 06 (see FIG. 3A). The examiner moves a cursor 100 on the display portion 06 to adjust a point indication of the tip end of the cursor 100 to a standard site on the image (for example, scleral spur), and performs a click operation.

Figure 3A:
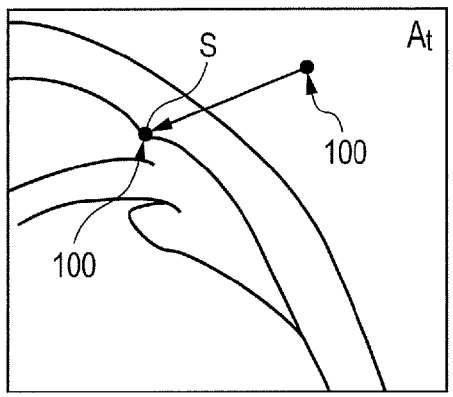
FIGS. 3A, 3B, 3C, 3D and 3E are diagrams illustrating a specific example in the case of quantitatively analyzing a chamber angle region of an eye to be inspected.
Figure 3B:
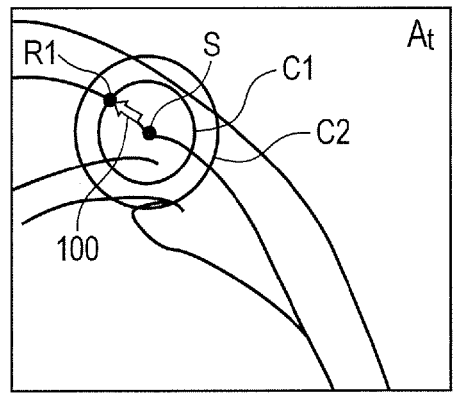

When a determination complete signal is input as described above, the signal processing portion 04 displays the standard point S at a designated position through the control portion 05, and displays circles C1 and C2 with the standard point S being the center (see FIG. 3B). The circle C1 corresponds to a circle having a radius of 500 µm on the image, and the circle C2 corresponds to a circle having a radius of 750 µm on the image. When the tip end of the cursor 100 is placed on a circumference of the circles C1 and C2, a point is displayed at the designated position. In the case where the standard point S is a scleral spur, the position away frontward by 500 µm and 750 µm from the scleral spur is considered as a position suitable for evaluating an opening degree of a chamber angle.

The examiner operates the mouse 01 and determines the reference point R1 away from the standard point S by a predetermined distance (for example, 500 µm or 750 µm) along the posterior surface of the cornea. Here, the examiner adjusts the tip end of the cursor 100 to a crossing point between the circle C1 or the circle C2 and the posterior surface of the cornea, and performs a click operation. In this case, the examiner can arbitrarily select which of the circle C1 and the circle C2 is to be used.

Figure 3C:
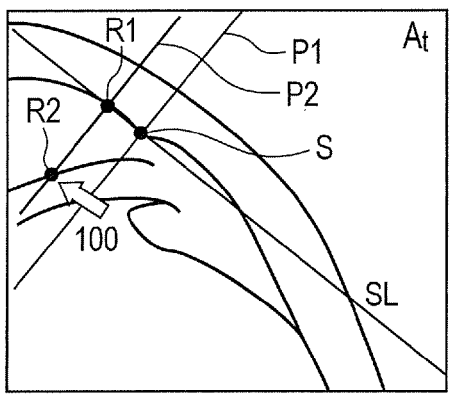
Figure 3D:
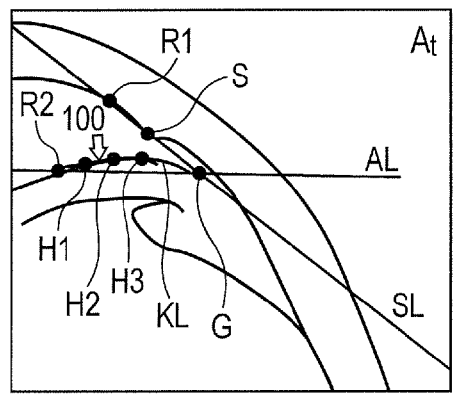

Here, when a determination complete signal is input, the signal processing portion 04 displays the reference point R1 at a designated position through the control portion 05, and displays the baseline SL connecting the standard point S to the reference point R1, and a normal P1 from the standard point S and a normal P2 from the reference point R1 with respect to the baseline SL (see FIG. 3C). It is preferred that the normal P1 be placed perpendicularly to the baseline SL, and a crossing angle thereof be defined to be substantially perpendicular with an allowance in accordance with an eye to be inspected.

Next, the process shifts to the iris reference point determination step S206. The examiner operates the mouse 01 to determine the iris reference point R2 at which the normal P2 and the anterior surface of the iris cross each other (see FIG. 3C).

Next, the process shifts to the iris approximated line setting step S207. The iris approximated line setting step includes: a step of determining two or more iris approximated points (for example, H1, H2, H3) on the anterior surface of the iris (see FIG. 3D); an iris approximated line setting step of determining an iris approximated line (for example, KL) passing through the iris reference point and the multiple iris approximated points; an angle recess reference point determination step of displaying on the display portion 06 and determining an angle recess reference point (for example, reference point G) at which the iris approximated line and the baseline cross each other; and an auxiliary line display step of displaying an auxiliary line (for example, an auxiliary line AL) passing through the iris reference point R2 and the angle recess reference point G on the display portion 06.

The iris approximated line setting step S207 is described in detail. First, the examiner operates the mouse 01 to adjust the tip end of the cursor 100 successively along the anterior surface of the iris from the iris reference point R2 toward the angle recess, and performs a click operation to determine two or more iris approximated points (H1, H2, H3). The clicked points are displayed on the display portion 06 by the control portion 05. In this embodiment, it is difficult to view the tip end of a chamber angle due to the problem of an invasion depth of the OCT, and hence, the iris approximated point is determined up to the tip end of a portion in which segmentation of an iris is performed.

When a determination complete signal of an iris approximated point is input, the signal processing portion 04 performs spline interpolation passing through the iris reference point R2 and the multiple iris approximated points (H1, H2, H3), and displays, on the display portion 06 through the control portion 05, the iris approximated line KL obtained by extrapolating the interpolated curve until the curve crosses the baseline SL, and determines the iris approximated line KL. In the present invention, the step from the determination of the iris reference point R2 to the determination of an approximated line that is a curve which approximates the shape of the anterior surface of the iris therealong through use of spline interpolation or the like corresponds to a first determination step, and the first determination step is performed in a module region that functions as a first determination unit or an approximated line determination unit in the signal processing portion 04. Further, the step of determining an approximated line extended part by extrapolating the curve that is the interpolated approximated line until the curve crosses the baseline SL to extend the approximated line corresponds to a second determination step, and the second determination step is performed in a module region that functions as a second determination unit in the signal processing portion 04. The obtained approximated line and the approximated line extended part are collectively defined as the iris approximated line KL, and an opening degree of the anterior chamber angle is calculated by a calculation step using the iris approximated line KL. The iris approximated line KL is determined in a module region that functions at a time of determination of an iris approximated line, and the calculation step is performed in a module region that functions as a calculation unit in the signal processing portion 04. Further, an opening degree of the anterior chamber angle of an eye to be inspected using information on the iris approximated line is calculated in a module region that functions as a chamber angle opening degree calculation unit in the signal processing portion 04.

As a method of interpolating and approximating an anterior surface of the iris, the method of performing spline interpolation has been described, but the anterior surface of the iris may be approximated with a circle or other interpolation lines and approximated lines may be used. Further, a point at which the iris approximated line and the baseline cross each other is displayed on the display portion 06 and determined as an angle recess reference point (for example, reference point G), and an auxiliary line (for example, auxiliary line AL) passing through the iris reference point R2 and the angle recess reference point G is displayed on the display portion 06 and determined. Further, it is preferred that the above-mentioned baseline SL and the like be displayed with the illustrated indication objects so as to be overlapped with the anterior ocular segment tomographic image, but the indication objects may be overlapped with the image with an arrow, a dotted line, a change in hue, or the like, or displayed separately from the image. Those indication objects are selected and displayed by a module region that functions as a display control unit for displaying the indication objects on the display portion 06 that is a display unit in the present invention.

The case where it is difficult to view a chamber angle is described in this embodiment. The reason why it is difficult to view a chamber angle is derived from the OCT. Specifically, in the case of using a light source having a wavelength of about 800 to 1,100 nm, light absorption by pigments such as hemoglobin and melanine contained in an eyeball tissue is large, and hence, light from the OCT light source may be attenuated before reaching a chamber angle. Therefore, if a light source having a wavelength of about 1,300 nm is used, light absorption by an eyeball tissue is reduced to enable a chamber angle to be viewed clearly. However, the wavelength to be mainly used for a posterior ocular segment OCT is 800 to 1,100 nm so as to ensure resolution, and an anterior ocular segment is generally acquired using a light source having a wavelength of about 800 to 1,100 nm in the case of measuring the anterior ocular segment together with the posterior ocular segment OCT. Further, even when a light source having a wavelength of about 800 to 1,100 nm is used, an eyeball pigment varies depending on the subject, and in some cases, a chamber angle may be viewed regarding a subject having a pale pigment.

In the case where a chamber angle is viewed clearly, that is, in the case where a boundary of the inner surface of the cornea is connected to a boundary of the anterior surface of the iris in the segmentation 5103 by the image processing portion, the iris approximated line setting step may not be performed.

In this case, chamber angle parameters are calculated by a general method in the chamber angle parameter calculation step described below through use of boundary information on each region of the anterior ocular segment obtained in the segmentation 5103.

After that, the examiner adjusts the cursor 100 to a Finish indication below the image At and performs a click operation.

The chamber angle parameter calculation step S208 is described in detail.

Figure 3E:
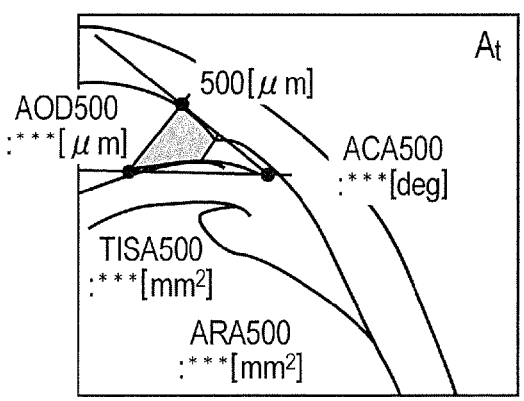

Here, when a determination complete signal is input, the signal processing portion calculates various parameters regarding an opening degree of a chamber angle and displays the calculation results on the display portion 06 (see FIG. 3E).

Various parameters are calculated as follows. An angle opening distance (AOD) 500 is calculated as a length of a line segment connecting the cornea reference point R1 to the iris reference point R2. In this case, the AOD 500 is a parameter representing a distance (unit: μm) between a point 500 μm forward from the scleral spur along the posterior surface of the cornea and a point at which a straight line drawn perpendicularly from the point crosses the anterior surface of the iris. Further, an anterior chamber angle (ACA) is calculated as a chamber angle formed by the baseline SL and the auxiliary line AL. In this case, the ACA is a parameter representing a chamber angle (unit: degree) formed by points at both ends of the AOD 500 and the angle recess. Further, an angle recess area (ARA) 500 is calculated as an area surrounded by a line segment of the AOD 500, a line segment of the baseline SL, and the iris approximated line KL. In this case, the ARA 500 is a parameter representing an area (unit: mm²) of a portion surrounded by the line segment of the AOD 500, the posterior surface of the cornea up to the angle recess, and the anterior surface of the iris. Further, a trabecular iris space area (TISA) 500 is calculated as an area of a portion to be in a region surrounded by the line segment of the AOD 500, a straight line drawn from the scleral spur in parallel to the line segment of the AOD 500, the baseline SL, and the iris approximated line KL (see shaded portion of FIG. 3E). The TISA 500 is a parameter representing an area (unit: mm²) of a portion indicated by a shaded area of a portion surrounded by the line segment of the AOD 500, a straight line drawn from the scleral spur in parallel to the line segment of the ADO 500, the posterior surface of the cornea, and the iris approximated line KL.

In the case where the chamber angle is viewed for the calculation of the ARA 500 and the TISA 500, a boundary of the anterior surface of the iris obtained in the segmentation 5103 is used instead of the iris approximated line KL.

(Output: S110)

When forming and analysis of each image is ended in the signal processing portion 04, the control portion 05 generates output information based on the result and outputs and displays the output information on the display portion 06. FIG. 3E corresponds to an example of a display screen of the output.

Further, in response to a request from the operator, the printer 07 prints the output screen formed by the signal processing portion 04, and the analysis result of the image based on the signal from the control portion 05.

With the above-mentioned configuration, even in the case where it is difficult to view a chamber angle and the shape of the anterior surface of the iris is curved, the chamber angle parameters such as the ARA 500 and the TISA 500 can be determined accurately.

Further, according to the procedure of Japanese Patent Application Laid-Open No. 2011-147611, an auxiliary line positioned on an anterior surface of the iris is determined manually, and hence, in the case where it is difficult to view the vicinity of a chamber angle, calculated values of various parameters tend to vary depending on the examiner. However, according to this embodiment, an auxiliary line positioned on an anterior surface of the iris is determined uniquely, and hence variation depending on the examiner is also suppressed.

In the above description, the multiple determination steps to be performed as preconditions for the chamber angle analysis are divided to enable the determination successively, and hence, the determination operation by the examiner becomes easy. Note that, the determination of a baseline in contact with the inner surfaces of the cornea and the sclera in the anterior ocular segment tomographic image is not limited to the determination of a straight line, and a curve along the inner surfaces of the cornea and the sclera in the anterior ocular segment tomographic image may be determined.

Further, although the examiner performs determination manually in the above-mentioned baseline determination step S205, the inner surfaces of the cornea and the sclera on an image may be detected by image processing to determine a baseline. Further, only the determination of a standard point may be performed manually. Further, similarly, the anterior surface of the iris on an image may be detected by image processing to determine an iris reference point in the iris reference point determination step S206.

(Other Embodiment)

Further, the present invention can be also realized by executing the following process. Specifically, software (program) for realizing functions of the embodiment described above is supplied to a system or an apparatus via a network or various storage media, and a computer (CPU, MPU, or the like) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2012-082211, filed Mar. 30, 2012, and No. 2013-009239 filed Jan. 22, 2013 which are hereby incorporated by reference herein in their entirety.

What is claimed is:

1. An analysis method for analyzing an anterior ocular segment tomographic image of an eye to be inspected, the analysis method comprising:
   a baseline determining step of determining a baseline corresponding to an inner surface of a cornea and an inner surface of a sclera of the anterior ocular segment in the anterior ocular segment tomographic image;
   an approximated curved line determining step of determining an approximated curved line that approximates a shape of an anterior surface of an iris of an anterior ocular segment of the eye to be inspected, corresponding to the anterior surface of the iris in the anterior ocular segment tomographic image;
   an extended curved line determining step of determining a curved line extended part obtained by extending the approximated curved line until the approximated curved line crosses the baseline;
   a position calculating step of calculating a position at which the curved line extended part crosses the baseline; and
   a value calculating step of calculating a chamber angle parameter value of the anterior ocular segment based on the calculated position at which the curved line extended part crosses the baseline.

2. An analysis method according to claim 1, further comprising a step of determining an iris reference point at which a substantial normal to the baseline and the anterior surface of the iris cross each other,
   wherein the approximated curved line determining step comprises a step of determining the approximated curved line based on the iris reference point.

3. An analysis method according to claim 1, further comprising:
   a step of determining a standard point in the inner surface of the cornea and the inner surface of the sclera of the anterior ocular segment in the anterior ocular segment tomographic image;
   a step of determining a reference point away from the standard point by a predetermined distance along the inner surface of the cornea; and
   a step of determining a line connecting the standard point to the reference point as the baseline.

4. An analysis method according to claim 3, wherein the approximated curved line determining step comprises a step of determining, as the approximated curved line, a line from the reference point toward an angle recess of the anterior ocular segment along the anterior surface of the iris.

5. An analysis method according to claim 3, further comprising an iris reference point determining step of determining an iris reference point at which a substantial normal to the baseline and the anterior surface of the iris cross each other,
wherein the position calculating step comprises a step of calculating, as an opening degree of the chamber, an area in a region connecting the reference point, the iris reference point, and a crossing point of the curved line extended part and the baseline.

6. An analysis method according to claim 1, further comprising displaying an indication object representing the baseline on a display portion so that the indication object is overlapped with the anterior ocular segment tomographic image.

7. An analysis method according to claim 1, further comprising displaying an indication object representing the curved line extended part on a display portion so that the indication object is overlapped with the anterior ocular segment tomographic image.

8. An analysis method according to claim 1, further comprising a step of displaying, on a display portion, an indication object representing the calculated position at which the curved line extended part crosses with the baseline, so that the indication object is overlapped with the anterior ocular segment tomographic image.

9. An analysis method according to claim 1, further comprising a step of displaying, on a display portion, the calculated position at which the curved line extended part crosses with the baseline.

10. A non-transitory tangible medium having recorded thereon a program for causing a computer to perform each step of the analysis method according to claim 1.

11. An analysis method according to claim 1, wherein the shape of the anterior surface of the iris is a curved shape, and
wherein the approximated curved line is determined so as to follow the curved shape of the anterior surface of the iris.

12. An analysis method according to claim 1, further comprising a step of determining an iris reference point at which a straight line crossing with the baseline and the anterior surface of the iris cross each other; and
a step of designating a plurality of positions other than the iris reference point,
wherein the approximated curved line determining step comprises a step of determining the approximated curved line based on the iris reference point and the designated plurality of positions.

13. An analysis method according to claim 1, further comprising a tomographic image acquiring step of acquiring the anterior ocular segment tomographic image of the eye to be inspected by using a tomographic image acquiring unit connected with an optical coherent tomographic apparatus in a state capable of communicating with each other.

14. An analysis method according to claim 1, wherein in the value calculating step, at least one of an anterior chamber angle (ACA) and an angle recess area (ARA) is calculated as the chamber angle parameter value.

15. An analysis apparatus for analyzing an anterior ocular segment tomographic image of an eye to be inspected, the analysis apparatus comprising:
a baseline determining unit configured to determine a baseline corresponding to an inner surface of a cornea and an inner surface of a sclera of the anterior ocular segment in the anterior ocular segment tomographic image;
an approximated curved line determining unit configured to determine an approximated curved line that approximates a shape of an anterior surface of an iris of an anterior ocular segment of the eye to be inspected, corresponding to the anterior surface of the iris in the anterior ocular segment tomographic image;
an extended curved line determining unit configured to determine a curved line extended part obtained by extending the approximated curved line until the approximated curved line crosses the baseline;
a position calculating unit configured to calculate a position at which the curved line extended part crosses the baseline; and
a value calculation unit configured to calculate a chamber angle parameter value of the anterior ocular segment based on the calculated position at which the curved line extended part crosses the baseline.

16. An analysis apparatus according to claim 15, further comprising an iris reference point determination unit configured to determine an iris reference point at which a substantial normal to the baseline and the anterior surface of the iris cross each other,
wherein the approximated curved line determining unit determines the approximated curved line based on the iris reference point.

17. An analysis apparatus according to claim 15, further comprising:
a unit for determining a standard point in the inner surface of the cornea and the inner surface of the sclera of the anterior ocular segment in the anterior ocular segment tomographic image;
a unit for determining a reference point away from the standard point by a predetermined distance along the inner surface of the cornea; and
a unit for determining a line connecting the standard point to the reference point as the baseline.

18. An analysis apparatus according to claim 17, wherein the approximated curved line determining unit determines, as the approximated curved line, a line from the reference point toward an angle recess of the anterior ocular segment along the anterior surface of the iris.

19. An analysis apparatus according to claim 17, further comprising an iris reference point determination unit for determining an iris reference point at which a substantial normal to the baseline and the anterior surface of the iris cross each other,
wherein the position calculation unit calculates, as an opening degree of the chamber angle, an area in a region connecting the reference point, the iris reference point, and a crossing point of the curved line extended part and the baseline.

20. An analysis apparatus according to claim 15, further comprising a display control unit for displaying an indication object representing the baseline on a display portion so that the indication object is overlapped with the anterior ocular segment tomographic image.

21. An analysis apparatus according to claim 15, further comprising a display control unit for displaying an indication object representing the curved line extended part on a display portion so that the indication object is overlapped with the anterior ocular segment tomographic image.

22. An analysis apparatus according to claim 15, further comprising a display control unit for displaying, on a display portion, an indication object representing the calculated position at which the curved line extended part crosses with baseline, so that the indication object is overlapped with the anterior ocular segment tomographic image.

23. An analysis apparatus according to claim 15, further comprising a display control unit for displaying, on a display portion, the calculated position at which the curved line extended part crosses with baseline.

24. An analysis apparatus according to claim 15, wherein the shape of the anterior surface of the iris is a curved shape, and
 wherein the approximated curved line determining unit determines the approximated curved line so as to follow the curved shape of the anterior surface of the iris.

25. An analysis apparatus according to claim 15, further comprising an iris reference point determination unit configured to determine an iris reference point at which a straight line crossing with the baseline and the anterior surface of the iris cross each other; and
 a designating unit configured to designate a plurality of positions other than the iris reference point,
 wherein the approximated curved line determining unit comprises a unit configured to determine the approximated curved line based on the iris reference point and the designated plurality of positions.

26. An analysis apparatus according to claim 15, further comprising a tomographic image acquiring unit which is connected with an optical coherent tomographic apparatus in a state of being capable of communicating with each other, wherein the tomographic image acquiring unit is configured to acquire the anterior ocular segment tomographic image of the eye to be inspected.

27. An analysis apparatus according to claim 15, wherein the value calculation unit calculates at least one of an anterior chamber angle (ACA) and an angle recess area (ARA) as the chamber angle parameter value.

28. An analysis method for analyzing an anterior ocular segment tomographic image of an eye to be inspected, the analysis method comprising:
 a baseline determining step of determining a baseline corresponding to an inner surface of a cornea and an inner surface of a sclera of the anterior ocular segment in the anterior ocular segment tomographic image;
 an approximated curved line determining step of determining an approximated curved line that approximates a shape of an anterior surface of an iris of an anterior ocular segment of the eye to be inspected, corresponding to the anterior surface of the iris in the anterior ocular segment tomographic image; and
 a value calculating step of calculating a chamber angle parameter value of the anterior ocular segment based on the baseline and the approximated curved line.

29. A non-transitory tangible medium having recorded thereon a program for causing a computer to perform each step of the analysis method according to claim 28.

30. An analysis method according to claim 28, wherein in the value calculating step, at least one of an anterior chamber angle (ACA) and an angle recess area (ARA) is calculated as the chamber angle parameter value.

31. An analysis method according to claim 28, wherein in the value calculating step, at least one of an angle opening distance (AOD) and a trabecular iris space area (TISA) is calculated as the chamber angle parameter value.

32. An analysis apparatus for analyzing an anterior ocular segment tomographic image of an eye to be inspected, the analysis apparatus comprising:
 a baseline determining unit configure to determine a baseline corresponding to an inner surface of a cornea and an inner surface of a sclera of the anterior ocular segment in the anterior ocular segment tomographic image;
 an approximated curved line determining unit configured to determine an approximated curved line that approximates a shape of an anterior surface of an iris of an anterior ocular segment of the eye to be inspected, corresponding to the anterior surface of the iris in the anterior ocular segment tomographic image; and
 a value calculating unit configure to calculate a chamber angle parameter value of the anterior ocular segment based on the baseline and the approximated curved line.

33. An analysis apparatus according to claim 32, wherein the value calculation unit calculates at least one of an anterior chamber angle (ACA) and an angle recess area (ARA) as the chamber angle parameter value.

34. An analysis apparatus according to claim 32, wherein the value calculation unit calculates at least one of an angle opening distance (AOD) and a trabecular iris space area (TISA) as the chamber angle parameter value.

* * * * *